United States Patent [19]
Compton

[11] Patent Number: 6,071,290
[45] Date of Patent: Jun. 6, 2000

[54] SURGICAL CLIP SET

[76] Inventor: Jeffrey Spencer Compton, 10 Derby Street, Penrith, NSW, 2750, Australia

[21] Appl. No.: 09/043,077

[22] PCT Filed: Sep. 24, 1996

[86] PCT No.: PCT/AU96/00600

§ 371 Date: Mar. 5, 1998

§ 102(e) Date: Mar. 5, 1998

[87] PCT Pub. No.: WO97/11645

PCT Pub. Date: Apr. 3, 1997

[30] Foreign Application Priority Data

Sep. 26, 1995 [AU] Australia ................... PN5622

[51] Int. Cl.⁷ ................................................. A61B 17/08
[52] U.S. Cl. ........................................... 606/151; 606/155
[58] Field of Search ................................... 606/151, 155, 606/156, 157, 142–143; 128/845

[56] References Cited

U.S. PATENT DOCUMENTS

| | | | |
|---|---|---|---|
| 3,713,533 | 1/1973 | Reimels | 606/143 |
| 4,076,120 | 2/1978 | Carroll | 606/143 |
| 4,361,229 | 11/1982 | Mericle | 606/143 |
| 4,791,707 | 12/1988 | Tucker | 606/143 |

FOREIGN PATENT DOCUMENTS

| | | |
|---|---|---|
| 85988/91 | 4/1992 | Australia . |
| 1345394 | 1/1974 | United Kingdom . |
| 2023216 | 12/1979 | United Kingdom . |

*Primary Examiner*—Michael A. Brown
*Attorney, Agent, or Firm*—Abelman, Frayne & Schwab

[57] ABSTRACT

A surgical clip set including an elongated main member, transversely extending stabilizer members at or adjacent each end of the main body. A plurality of surgical clips extending outwardly from each side of the main member with each clip being detachably secured to the main member and all the clips being located within the transversely extending stabilizer members.

6 Claims, 2 Drawing Sheets

SURGICAL CLIP SET

TECHNICAL FIELD

This invention relates to surgical clips and more particularly to a surgical clip set having a carrier and a plurality of surgical clips detachably secured thereto.

BACKGROUND ART

For the sake of convenience, the invention will be described in relation to Raney style scalp clips which are used in neurosurgery but it is to be understood that the invention is not limited thereto as it may be applied to similar surgical clips.

Hitherto, Raney style scalp clips have been supplied as a group of, say, ten individual clips in a sterilised package. When required during an operating procedure, the package is opened and the individual clips emptied onto a convenient surface in the operative set up. This emptying of the package results in a random orientation of the individual clips which creates alignment difficulties for the surgeon or nurse as attempts are made to load a clip onto the applicating forceps. (see FIG. 1)

SUMMARY OF THE INVENTION

According to the invention there is provided a surgical clip set comprising:

(i) an elongated main member;
(ii) transversely extending stabiliser members at or adjacent each end of the main member; and
(iii) a plurality of surgical clips extending outwardly from each side of the main member with each clip being detachably secured to the main member and all the clips being located within the transversely extending stabiliser members.

BRIEF DESCRIPTION OF THE DRAWINGS

In order that the invention may be more readily understood and put into practical effect, reference will now be made to the accompanying drawings in which.

BEST MODE FOR CARRYING OUT THE INVENTION

Figure 2:
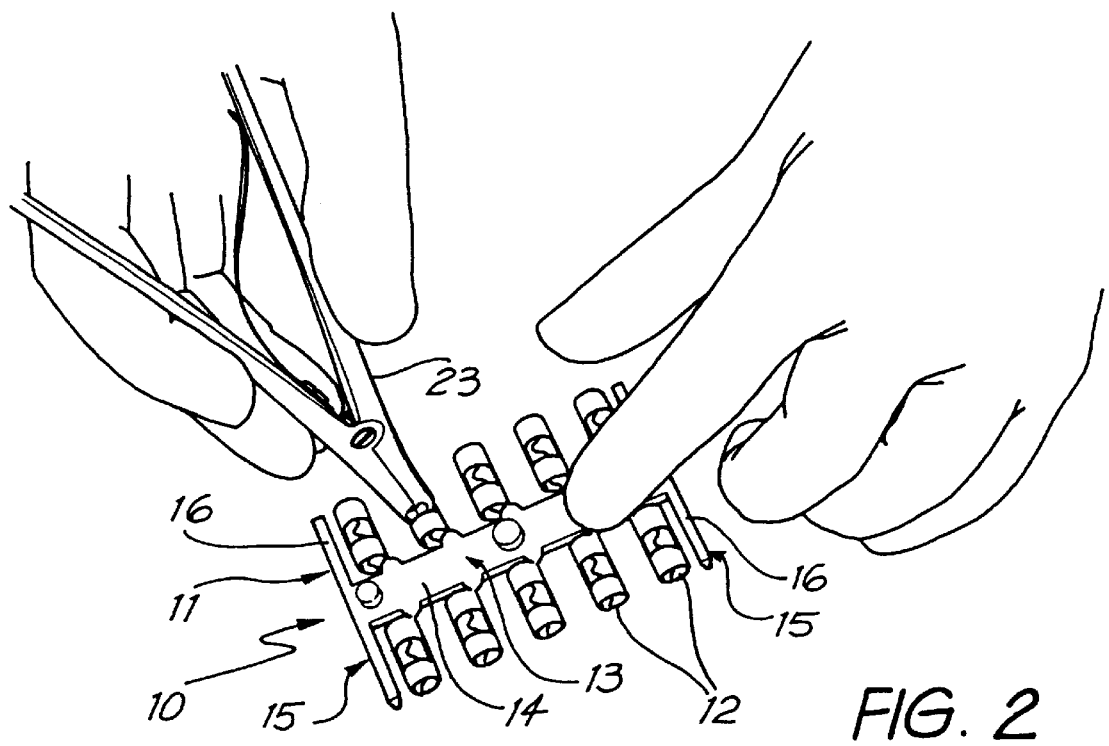
FIG. 2 is a view similar to FIG. 1 showing the surgeon loading a Raney clip onto an applicating forcep from a surgical clip set in accordance with one embodiment of the invention.
Figure 5:
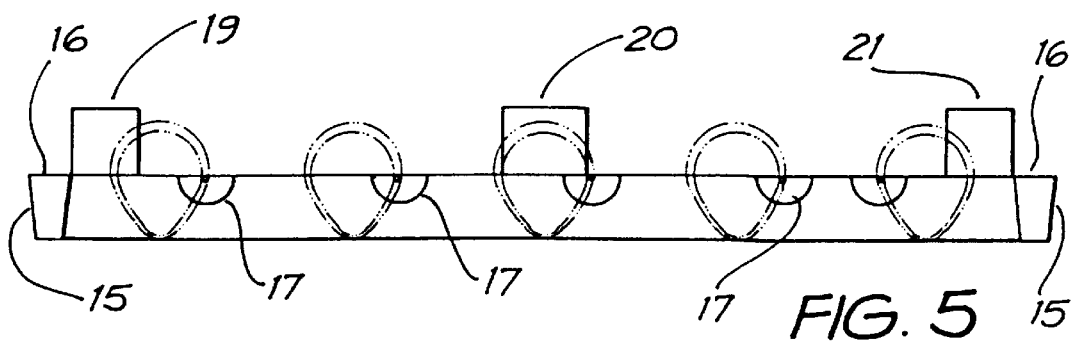

The surgical clip set 10 shown in FIG. 2 comprises a carrier 11 and a plurality of Raney style scalp clips 12. The carrier 11 includes an elongated main member 13 having a generally planar upper face 14. Extending transversely outwardly from each end of the main member 13 there is a stabilising bar 15 as can be seen in FIG. 5. In this instance, the upper face 16 of each stabiliser bar 15 is coplanar with the upper face 14 of the main member 13.

In the embodiment shown in FIGS. 2 to 5, the main member 13 is 75 mm long and each stabiliser bar 15 is 47 mm long. In between each stabiliser bar 15 there are five Raney style scalp clips on each side of the main member 13 with all the clips 12 being located within the area bounded by the transversely extending stabiliser members 15. Projecting outwardly from each side of the main member 13 there are five spaced apart anchor points 17 to which the clips 12 are attached by an easily breakable joining portion 18 (see FIG. 4).

Figure 3:
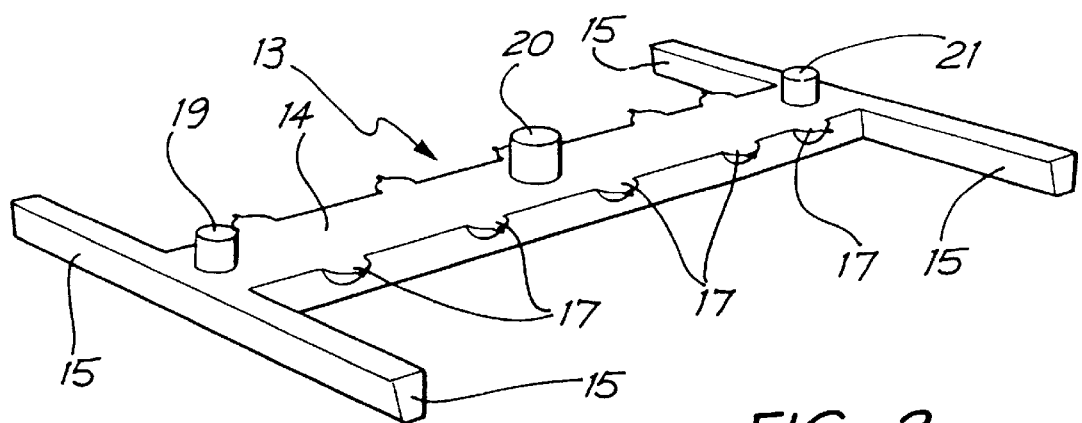
FIG. 3 is a perspective view of the carrier portion of the surgical clip set shown in FIG. 2 with the clips removed.

As can be best seen in FIG. 3, on the upper face 14 of the main member 13 there are three upwardly projecting cylindrical stubs 19, 20 and 21. The central stub 20 represents the sprue of the mould in which the surgical clip set 10 is made and the outer stubs 19 and 21 are formed to protect the clips from the package in which they are enclosed ready for distribution.

Figure 1:
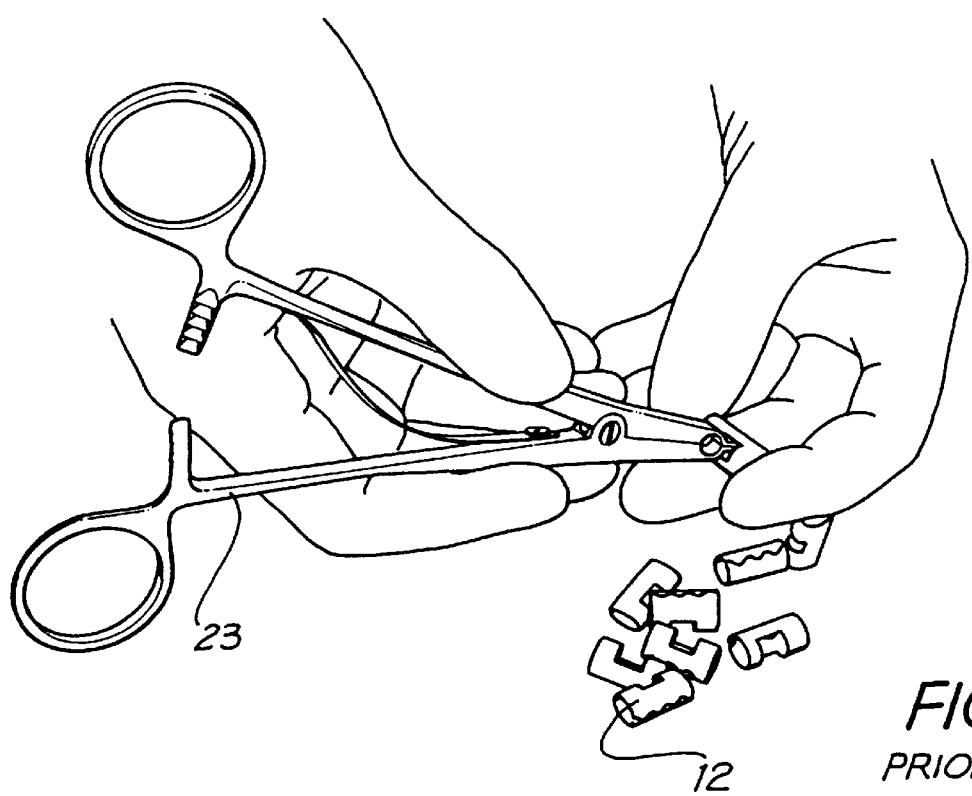
FIG. 1 is a perspective view of a surgeon loading a surgical clip onto applicating forceps with the clips randomly orientated in accordance with the prior art.
Figure 4:
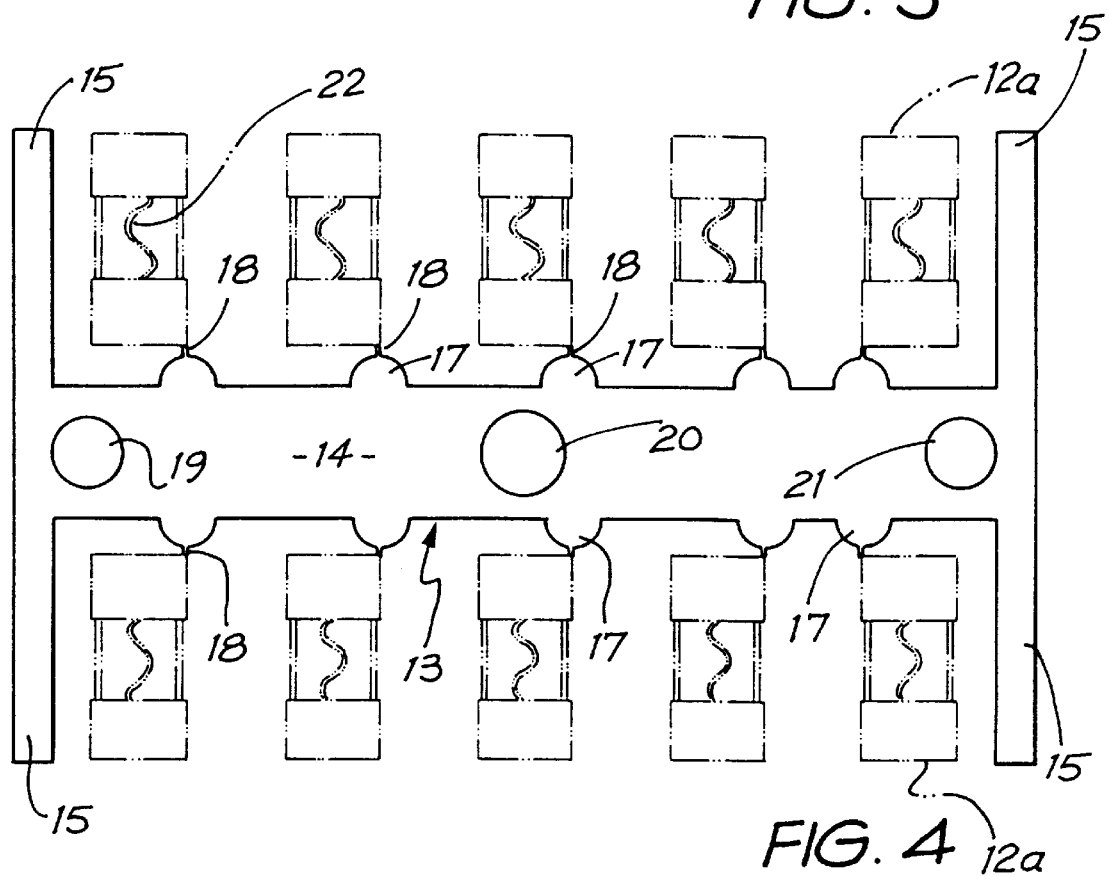
FIG. 4 is a plan view of the surgical clip set shown in FIG. 2; and, FIG. 5 is a side elevational view of the surgical clip set shown in FIG. 2.

The surgical clip set 10 of the carrier 11 and the plurality of clips 12 may be made from any suitable material such as acetyl copolymer or a variety of other plastics materials to provide a one-piece device. As can be seen in FIG. 4, the clips 12 are orientated with respect to the central member 13 with an opening 22 in the mid portion of the clip 12 for the applicator forceps 23 being perpendicular to the central member 13 and pointing upwards in relation to the central member 13. The manner in which the applicator forceps 23 engage the clips 12 can be seen in FIGS. 1 and 2. Each clip 12 is of hollow cylindrical form with mating clip faces 24, 25 opposite the forceps opening 22.

As can be seen in FIG. 4, the right hand clips 12a are orientated in the opposite way to the other clips so that the associated joining portions 18 are not adjacent the stabiliser member 15.

The clips 12 are within the imaginary boundaries defined by the top of the studs 19, 20 and 21, the bottom face of the main member 13 and the stabiliser member 15, as can be seen in FIG. 5.

The use of the surgical clip set 10 of the carrier 11 and clips 12 allows the Raney style scalp clips 12 to be safely located in one part of the operative set up thereby preventing their loss amongst other surgical instruments. The surgical clip set 10 allows the clips 12 to be easily and quickly loaded onto the applying forceps 23 adding ease and convenience to this phase of the operating procedure as well as saving time and reducing bleeding from scalp wounds.

INDUSTRIAL APPLICABILITY

The surgical clip set of the invention provides a surgeon or nurse with clips in the required orientation for attachment to forceps.

I claim:

1. A surgical clip set comprising:

(i) an elongated main member;
(ii) transversely extending stabiliser members at or adjacent each end of the main member; and
(iii) a plurality of surgical clips extending outwardly from each side of the main member with each clip being detachably secured to the main member and all the clips being located within the transversely extending stabiliser members.

2. A surgical clip set according to claim 1 wherein the main member has a plurality of spaced apart anchor points projecting transversely outwardly and wherein a clip is attached to an anchor point by an easily breakable joining portion.

3. A surgical clip set according to claim 1 wherein the main member has an upper face and a lower face and wherein the upper face has a plurality of stubs projecting outwardly thereof.

4. A surgical clip set according to claim 3 wherein the clips are located within an imaginary volume defined by the outer ends of the stubs, the lower face of the main member and the stabiliser members.

5. A surgical clip set according to claim 1 wherein the clips, main member and stabiliser members are formed from a moulded plastics material.

6. A surgical clip set according to claim 5 wherein the plastics material is acetyl copolymer.

* * * * *